United States Patent [19]

DiDomenico

[11] Patent Number: 4,714,462

[45] Date of Patent: Dec. 22, 1987

[54] POSITIVE PRESSURE PROGRAMMABLE INFUSION PUMP

[75] Inventor: Robert A. DiDomenico, Norfolk, Mass.

[73] Assignee: Intermedics Infusaid, Inc., Norwood, Mass.

[21] Appl. No.: 824,986

[22] Filed: Feb. 3, 1986

[51] Int. Cl.⁴ .............................................. A61M 5/14
[52] U.S. Cl. ....................................... 604/67; 604/141; 604/891
[58] Field of Search ............. 604/65, 67, 66, 151–154, 604/131–133, 890, 891, 141; 128/DIG. 12, DIG. 13; 417/472–473

[56] References Cited

U.S. PATENT DOCUMENTS

| | | | |
|---|---|---|---|
| 4,077,405 | 3/1978 | Haerten et al. | 604/66 |
| 4,265,241 | 5/1981 | Portner et al. | 604/131 |
| 4,443,218 | 4/1984 | De Cant, Jr. et al. | 604/67 |
| 4,447,224 | 5/1984 | De Cant, Jr. et al. | 604/67 |
| 4,486,190 | 12/1984 | Reinicke | 604/67 |
| 4,525,165 | 6/1985 | Fischell | 604/891 |
| 4,557,726 | 12/1985 | Reinicke | 604/67 |

Primary Examiner—Stephen C. Pellegrino
Attorney, Agent, or Firm—Sughrue, Mion, Zinn, Macpeak & Seas

[57] ABSTRACT

A positive pressure positive displacement implantable infusion pump. A positive pressure fluid reservoir maintains infusate for delivery by a positive pressure displacement pump. Infusate is drawn by the pump into a drug pressurant chamber. A check valve prevents backflow into the reservoir. The check valve may independently establish a basal flow rate by not completely sealing in the forward flow direction. The pump pulses to expel and fill the chamber thereby establishing the flow rate, basal or bolus through a restrictor interposed between the chamber and the infusion site. The pump may run in open loop, pre-programmed or externally programmed modes of operation.

23 Claims, 2 Drawing Figures

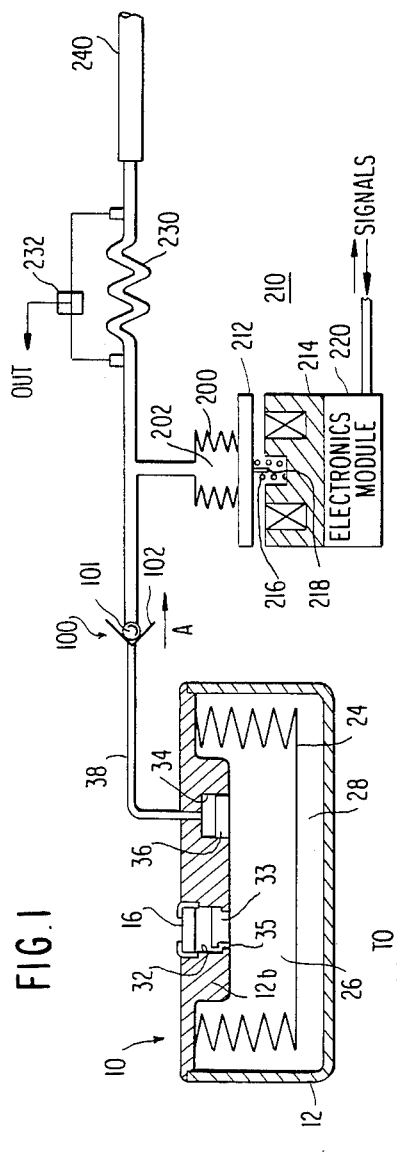
FIG. 1
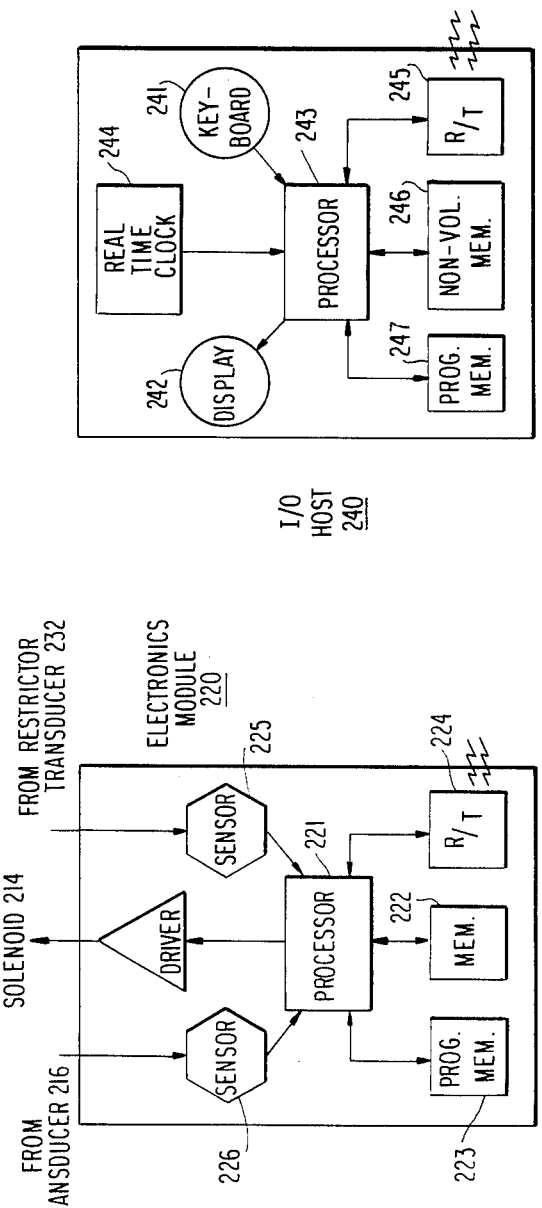

POSITIVE PRESSURE PROGRAMMABLE INFUSION PUMP

BACKGROUND OF THE INVENTION

This invention relates to an implantable infusion pump. In particular, it relates to a pump of the type which is programmable to dispense infusate with accordance with different flow rates while operating at positive pressure.

Implantable infusion pumps have been developed to the point of commercial and medical acceptance. Those devices are implantable in the human body and rely on a liquid/vapor equilibrium to maintain constant pressure on the drug which flows through a capillary in order to maintain a constant flow rate. These so called "constant flow" devices are used in a variety of medical applications, for example, to dispense chemotherapy drugs at a relatively constant flow rate. The technology represented by such constant flow devices is reported in Wright, "A Portable Slow Infusion Capsule", 177 J. physiol. 5P (1965) and in U.S. Pat. No. 3,731,681.

In situations where patients require adjustments in the dosage as a function of time constant flow pumps are inadequate. A typical example is diabetes where the quantity of medication, such as insulin, to be infused varies due to requirements of the patient. Fluctuations can occur on a daily basis or more randomly as a function of the ingestion of food. Consequently, to address the shortcomings of constant flow devices and obtain significant flexibility in dosage rates, research has been conducted into so called "implantable programmable" pumps. In the definition of system requirements dealing with such implantable programmable pumps, a device which will provide programmable bolus and basal flow rates over a wide dynamic range is a standing system requirement. This requirement can be set forth in a practical sense by reference to the treatment of diabetes. It is known that the amount of medication, typically insulin, to be infused per unit of time, should be adjusted at certain time intervals. A patient's requirements may fluctuate either at set, know rates or may vary abnormally, for example, by the ingestion of food or by other transitory conditions. Those conditions will call for the administration of a bolus dose of infusate. In the daily administration of insulin, however, the patient may require a basal dose that is supplanted by bolus doses at, for example, meal times. The difference in flow rates between basal and bolus doses may be quite large, in the orders of several times. Thus, a device to achieve proper flow rates over the spectrum of desired rates must have the ability to continuously infuse, at very low flow rates, yet provide, periodically, a substantially increased flow rate. Thus, the design criteria can be summarized as requiring, in the first instance, the ability for continuous, that is basal drug delivery which is adjustable to varying choices of flow rate. The choices should include wide ranges of flow rates to accommodate bolus requirements.

While the basic flow devices offer simplicity in operation and design and as complexity occurs, given the inherent intricacy of programmability, other problems occur such as power consumption, overall system life and failsafe operation.

The art is replete with a number of different implantable programmable pump concepts such as found in U.S. Pat. Nos. 3,894,538; 4,077,405; and 4,443,218. However, the diverse system requirements have not been fulfilled by any existing commercially available or proposed system. Such programmable pumps generally fall into two broad categories. The first are the so called negative pressure pumps which are typified by U.S. Pat. Nos. 4,482,346 and 4,486,190. Both of these prior art devices are solenoid activated negative pressure pumps. A diaphragm storage chamber maintains the drug to be infused in a chamber having a diaphragm which separates the drug from propellant, normally freon, maintained at negative pressure. A solenoid is activated driving an armature and a bellows pumping element. This displacement of the armature opens a check valve which draws drug from the storage chamber into a downstream pumping chamber. A restriction will prevent backflow in the outlet during this short period. When the pump chamber is full, the check valve closes and the solenoid is then de-energized. A spring force typically displaces the bellows into the chamber pumping the drug through a restrictor and into the patient. The bellows armature assembly comes to rest on the check valve to insure no backflow during the rest period, it being noted that the drug chamber pressure is below body pressure. The system operates at negative pressure to insure no forward flow during this rest period.

Negative pressure systems, while offering advantages in terms of accurate dosage and metering, suffer from two significant disadvantages. First, the ingestion of air into the system will stop drug flow. Thus expensive fill and empty apparatus is required for filling and recycling such devices. A more practical, serious problem, exists in the special handling required for negative pressure devices. The drugs used with such devices must be vacuum conditioned, thereby requiring that special steps be taken by those who are, in many cases, technically unsophisticated, and must be packaged and shipped with special care to maintain the vacuum conditioning. Consequently, while such devices offer theoretical technical advantages, in practice they suffer from significant practical disadvantages.

A second class of devices are the so-called positive pressure pumps in combination with an accumulator pump. Such are presented by U.S. Pat. Nos. 4,299,220 and 4,447,224. The device operates at a positive pressure, thereby obviating the problems of negative pressure devices. Given the fact that drug chamber pressure is above body pressure, a remote potential for an overdose of drug exists should all valves in line with the output fail open at the same time. An extremely high degree of safety can be achieved in such systems by redundant or failsafe valves and the addition of sensor/shutdown circuits. However, this means that significant costs are added to the system to address remote possibilities.

Consequently, within the art, a need exists for a reliable programmable pump pressure system that eliminates the problems existing in present designs.

Finally, the device should have the capacity to store in a drug storage reservoir a sufficient amount of infusate to obviate the need for frequent refill. Consequently, within this technology, there exists diverse system requirements which have not been fulfilled by any existing commercially available or proposed system.

SUMMARY OF THE INVENTION

Given the deficiencies in the prior art, it is an object of this invention to provide for a positive pressure, positive displacement implantable pump. This invention has the capability of pumping small, that is microliter, quantities of drug at a programmed rate. Simplicity of design, and therefore an improvement in safety is a primary aspect of this invention. The pump operates at positive pressure, thereby removing the handling and potential failure problems inherent in negative pressure designs. Moreover, the additional expense of components required to address remote failure possibilities in the valve-accumulator pump technology are overcome by this invention.

In its most basic form, the pump of this invention comprises a drug reservoir, a drug pressurant chamber, a check valve, a solenoid displacement pump and a high resistance flow restrictor. Sensors to monitor stroke and differential pressure are a part of the invention.

In operation, an electrical signal triggers the solenoid which causes a volume increase in the pumping chamber. Fluid for this displacement flows from a positive pressure drug reservoir through a check valve. Only a negligible amount of drug will backflow from the high resistance flow restriction which is located downstream from the pumping chamber. When the chamber is full the check valve, normally biased toward it seat by a spring, closes. The solenoid is then de-energized and the solenoid spring drives the pumping element into the pumping chamber increasing its pressure. The check valve, however, is closed so that the drug cannot flow back into the reservoir and, therefore flows through the flow restriction, into the catheter and thus to the infusion site. The check valve, in accordance with this invention, may operate at an opening pressure somewhat higher than the reservoir pressure or at an opening pressure that is some small percentage of the reservoir pressure such that between pumping cycles the valve either seals or provides a low forward flow rate. Such provides either no flow rate or a continuous basal flow between pumping cycles. In the first case, the time averaged flow rate is controlled strictly by the interval of the solenoid pulse, providing either a pulsatile basal flow or bolus flow, at the command of the program. In the second case, the solenoid pulse can augment the low basal flow in a pulsatile fashion, or override the low basal flow with a closely spaced series of pulses providing a bolus flow, again at the command of the program.

As indicated herein, system reliability and safety is a paramount design consideration. In the case of mechanical failure, an overdose of drug would be impossible. Such is prevented by the large resistance flow restrictor which is always in the path between the drug reservoir and the body. Consequently, the presence of the restrictor would limit drug flow rates to predetermined calculated low basal flow.

In such a system, feedback may be either in the form of differential pressure across the flow restrictor or, a displacement measurement of the pumping element or solenoid armature. The invention may also use both feedback techniques by comparing the stroke per unit time and the differential pressure change per unit time and match a signature of values or a map which may be stored in a ROM of predicted or actual values. The system operates by using sensors, matching of actual values to those previously stored to provide feedback to the system. Thus, by comparing actual values to a matrix of stored predicted values, the accuracy of the delivered quantity can be determined and adjusted. The adjustment is by varying the activation interval of the solenoid.

This invention will be described in greater detail by referring to the attached Figures and Description of the Preferred Embodiment which follows.

BRIEF DESCRIPTION OF THE DRAWING

FIG. 1 is a diagrammatic view illustrating the infusion system implanted in a living body in accordance with this invention; and FIG. 2 is a block diagram of the electronic components of this the preferred embodiment invention.

DESCRIPTION OF THE PREFERRED EMBODIMENT

Referring now to the figures, the apparatus forming the essential components of this invention can be defined as follows. It is understood that the entire device of FIG. 1 is implanted and the casing forming the housing has been omitted. A storage chamber 10 comprises the positive pressure drug reservoir in accordance with this invention. The second component is the check valve 100 which is interposed between the storage chamber 10 and a pumping chamber 200 having associated with it a drive mechanism 210 and electronics module 220. A flow restrictor 230 forms an outlet establishing fluid communication between the system as implanted and infusion site 240 in a living body under treatment.

The storage chamber 10 comprising the drug reservoir is illustrated in highly schematic form. This device may be similar to the drug reservoir in a commercially available unit such as an INFUSAID MODEL 100 or, 400 as manufactured by Intermedics-Infusaid, Inc. The device will be described herein only for an appreciation of the invention, it being understood that a commercially available component may be employed.

The storage chamber comprises a generally cylindrical housing 12 which contains the fluid to be infused. The path of fluid communication is established between the storage chamber 10 and infusion site 240 through the check valve 100 and the flow restrictor 230. This path is defined as the "forward flow" direction, that is from storage chamber to infusion site. The arrow A illustrates this direction.

In accordance with known techniques, when the infusate within the housing 12 is exhausted the system can be refilled by subcutaneous injection through a self-sealing septum 16 provided in an unobstructed surface portion of the housing 12. Thus, when the device is properly implanted, the septum 16 is located directly under the patients skin and is accessible via syringe. The container 12 is preferably small and without sharp corners. While not illustrated, appropriate suture points may be included. The container itself is made of a material which is compatible with the human system such as titanium. The container 12 contains a bellows 24 having an open end mounted to a top or header portion 12b in the container 12. The opposite end of the bellows is, as illustrated in FIG. 1, closed. The bellows, therefore, defines two chambers. The first, chamber 26 is inside the bellows while the second chamber 28 is outside the bellows yet still inside the housing 12.

The top portion or header 12 includes an entry port 32 which extends from the chamber 26 through the header 12b. A septum 16 closes the port 32. A porous needle stop 33 is positioned at the inner end of the port 32. As illustrated in the FIG. 1, when filled by syringe, the needle will rest at stop 33, however, the entry port 32 has a path of fluid communication 35 to the chamber 26.

Formed in the header 12b, is an exit port 34. Filter 36 may be included. This port communicates via an outlet tube 38 to establish fluid communication through the check valve 100. The outlet tube 38 must be sufficiently large to minimize any pressure drop between the drug reservoir and the pumping chamber to thereby reduce cavitation.

Outer chamber 28 is filled with a two-phase liquid which vaporizes at physiological temperatures so that it exerts a pressure on the bellows capsule 24 which tends to compress the bellows thereby reducing its volume. This, in turn, maintains positive pressure on the infusate in the drug reservoir 26, thereby expelling it through the exit port 34 and the outlet tube 38. The operation of such a two-phase fluid is well documented as set forth in Wright et al, supra and U.S. Pat. No. 3,731,681. By such techniques, infusate in the chamber 26 can be maintained at positive pressure yet dispensed at low flow rates to meet long term requirements. However, as set forth herein, while maintaining positive pressure, variations occur as a function of differences in temperature and pressure. Consequently, while the infusate in the drug chamber 26 can be maintained under positive pressure, the system is required to provide positive metering of infusate and provide both bolus and basal dosages. The additional structure illustrated in the FIG. 1 provides such positive control and safety.

The check valve 100 is designed to open and provide a flow of infusate as illustrated by the arrow A in FIG. 1 yet close to prevent any backflow during dispensing of the infusate from the chamber 200. The check valve 100 offers several advantages depending on the ultimate metering system to be employed. The check valve may be configured with a high operating pressure such that it positively seals between pumping cycles (to be discussed herein) and the system operates and provides infusate to the site 240 solely as a function of pumping cycles of the system. In this mode, the check valve 100 opens by differential pressure and infusate is drawn from chamber 26 into the pumping chamber 202. That is as the volume of chamber 202 increases, pressure drops across the valve to open it and deliver infusate into chamber 202. When chamber 202 is filled, the pressure equalizes across the valve and the valve closes.

Alternatively, the valve 100 may be configured to have a low operating pressure such that it provides a low flow rate irrespective of the pumping cycle of the system. By establishing this flow rate be a small predictable level, a continuous basal flow may be provided from the chamber 26 directly to the infusion site as a function of the positive pressure maintained in the drug reservoir 16 as a function of the two-phase fluid in chamber 28. This occurs by having the check valve 101 seated such that minimum displacement is needed to seal, but prior to sealing a low flow rate passes through the valve. It is noted that the pressure drop across the valve is small compared with the pressure drop across the restriction 230.

In accordance with this invention, a drug pressurant chamber 200 is provided in fluid communication with the drug reservoir 26. This chamber comprises a flexible bellows member having an internal cavity portion coupled to the conduit 38. Pumping chamber 200, therefore, can expand or contract thereby altering the volume of the cavity 202. Such expansion or compression is accomplished by having the pumping chamber 200 coupled or operably attached to an armature 212 which is a component part of a solenoid 214 comprising the displacement pump structure 210. The armature 212 is biased via a spring 216 in a direction to reduce the volume of the chamber 202. The solenoid is driven by an electronics module 220, to be described in detail herein.

In operation, an electrical signal to the electronics module 220 triggers the solenoid 214. The armature 212 is driven in a direction such that the volume 202 of the pumping chamber 200 is increased. Thus, as shown schematically, the armature would be driven downward. This causes a volume increase in chamber 202. Fluid from the pressurized drug reservoir 26 then flows through the check valve 100 into chamber 202. Given the presence of the restrictor 230, only a negligible volume of infusate will backflow from the flow restriction. When the chamber 202 is full, the check valve 100 which is biased by a spring (not illustrated) will close. The solenoid 214 is subsequently de-energized and the spring 216, now providing a bias force on the pumping element, armature 212, drives that element upward thereby increasing the pressure in chamber 202. At this time, the check valve 100 is closed and thus infusate cannot flowback into the reservoir 26. The pressure increase drives fluid through the flow restriction 230 and thus, into the infusion site 240.

The system may operate in various modes of operation. In an open loop mode, the flow rate to the infusate site 240 is controlled simply by a pre-programmed time rate of solenoid pulse cycles. If the check valve 100 is configured to seal, in an open loop mode, a continuous pulsatile basal flow is maintained by selecting a pulse interval for the solenoid to maintain sufficient pressure in the system to allow infusate to pass through the restrictor. The basal flow rate can also be established by having a low forward flow across the check valve 100 at all times except when the solenoid is activated. The flow rate can be determined as a function of the pressure drop across the restrictor 230. This is a function of the diameter of the restrictor, the viscosity of infusaid and the length of the restrictor tubing. Other techniques of establishing the desired resistance in the flow path can be employed by predetermining those physical limitations of the restrictor tubing, pressure differential can be ascertained and the flow rate accordingly determined. Such techniques are well known in the art.

To achieve a constant basal flow plus bolus flow, in an open loop mode, the solenoid pulse interval will decrease during that time frame when bolus flow is to be achieved. This creates increased pressure at the upstream portion of the restrictor thereby increasing the flow rate over that which has been previously predetermined to achieve basal flow. Consequently, in an open loop mode, the flow rate can be determined solely as a function of the interval of the solenoid pulses. This will achieve either a pulsatile basal flow or basal flow plus periodic bolus dosages. It also readily apparent that only bolus dosages may be administered in the same manner.

The system may also operate in a closed loop mode by sensing differential pressure across the flow restrictor 230. Thus, as illustrated in the figure a differential pressure transducer 232 would sense the pressure at the upstream and downstream portions of the flow restrictor 230 and provide a signal output to the electronics module 220. This output indicative of differential pressure across the restrictor and therefore flow rate in the system to the infusate site 240 is compared in the electronics module 220 with a signature of values or a map stored in a ROM of predicted or actual values. An output signal is provided from the electronics module 220 to the solenoid 214 to vary the flow rate, i.e. the pulse repetition rate is changed achieve proper flow rate. In this mode of operation a new instruction is provided to establish a new flow rate which is in turn a function of the pulse period of solenoid actuation.

Correspondingly, displacement transducer 218 can be used to sense movement of the armature 212 relative to the fixed solenoid 214. This provides an indication of volume of the pumping chamber 200. By providing a signal to the electronics module, compensated closed loop operation can be achieved in the same manner as in the determination of differential pressure across the restrictor.

Alternatively, the system in a closed loop mode can use signals from both differential pressure transducer 232 and the actual displacement of the pumping element 212. Such would compare the stroke per unit time relatively to the differential pressure change per unit time and matching those system operating characteristics to a signature of the two values stored in a ROM in the electronics module 220. By comparing actual values to a map of predicted values, the accuracy of the delivered quantity can be corrected by adjusting the flow rate instructed from the ROM.

FIG. 2 illustrates the electronics portion of this invention and is described in a block diagram form. It is understood that the electronics module 220 comprises a very small miniaturized component of the implantable system. The electronic module comprises a microprocessor 210 having associated of therewith a memory section 222 and a programmable memory of 223. The memory 222 is used to store processor operating software, data received from external sources and processor housekeeping functions. Programmable memory 223 is used to store the sequence of instructions to vary the solenoid pulse repetition rate.

A telemetry module 224 contains a receiver and transmitter and forms a communications link illustrated schematically between the module 220 and an external I/O device. The receiver section provides in input to the processor, receiving external signals for processing by the module. The transmitter section provides the output of the external host device.

Sensors 225 and 226 receive signals respectively from the restrictor transducer 232 and the transducer 261 indicative of pumping chamber or armature placement. Those two sensors provide inputs to the processor 221 for purposes of establishing new flow rate instructions. The electromechanical link from the module 220 to the solenoid is provided by a driver 227. The driver receives instructions from the processor 221 and delivers its output to the solenoid 214. That is, the driver output is series of pulses having a repetition rate to establish the driving cycle of the solenoid thereby establishing the flow rate through the system.

The miniaturization of the module 220 is well known in this technology. It will be appreciated by those of working skill that techniques to engineer similar programmable modules in pacemaker technology involving the same degree of computer miniaturization may be employed in the configuration of module 220. The battery power sources are not illustrated.

FIG. 2 also illustrates block diagram formation of the external I/O device 240. The size of that device is approximately that of a hand held calculator. In the same scale as a calculator, the device employs a keyboard 241 for inputting data and an alphanumeric display 242. Those devices are coupled to the processor 243 for purposes of input and display of various functional data.

The host device employs a real time clock 244. The clock is important in the context of this device to cycle instructions based on a 24-hour day. That is, variations in the flow rate which are programmed at meal times, periods of sleep and the like require a real time clock input.

In a manner similar to that of the electronics module 220, the I/O host device employs a receiver and a transmitter section 245 to provide basic I/O functions to the module 220, together with a nonvolatile memory 246 and a programmable memory 247. The programmable memory may be interchangeable so that the device 240 can find utility over a matrix of potential utilizations. That is, the programmable memory 247 may have instructions which are initialized to a particular patient or to a particular class of users. By interchanging of those instructions in a memory, the host device may find more generic utilization.

In operation, the system in a programmable mode receives instructions from the host 240 indicative of flow rates for a patient having the implanted device. Instruction data input from the receiver 224 to the processor 221 results in the delivery from the program memory 223 of an instruction comprising a pulse repetition sequence, that is a series of pumping instructions corresponding to input data. Such is then provided to the driver 227 for purposes of establishing a flow rate varying the pulse repetition rate of the solenoid 214. Regulation of the flow rate, that is monitoring externally can take place by having data from the sensor 225 and/or 226 delivered to the processor 221 which then outputs that flow rate data via the transmitter 224. Such, when received by the host 240 is displayed on display 242 providing a real time indication of the flow rate of the implanted system. To the extent that further regulation is required, new data is input on the keyboard 241, suitably processed and sent by the telemetry link 224-245 to the module 220. It is apparent that the device may be programmed either by patient himself or by an attending doctor. This flexibility in programming allows flow rate changes to be made as a function of those factors which would require an increased or decreased supply of infusate and not having to explant the device.

An important aspect of this invention is that if a mechanical failure occurs, a drug overdose to the infusion site 240, is impossible. The presence of the flow restrictor 230, which is always in the path between the drug reservoir 26 and the infusion site, would restrict the drug flow to a low basal flow in the case of leakage through the check valve 100.

It is apparent that modifications of this device may be made without departing from the essential scope of the invention.

What is claimed:

1. An infusion system for implantation in a living body comprising;
    a fluid reservoir maintaining a liquid for delivery to an infusion site under positive pressure with respect to body pressure at said infusion site;
    a drug pressurant chamber receiving fluid from said fluid reservoir;

a positive displacement pump to vary the volume of said drug pressurant chamber and thereby either fill said chamber by increasing its volume or pressurize said chamber to expel fluid from said chamber by reducing its volume;

valve means interposed between said reservoir and said chamber to prevent backflow of said fluid into said reservoir;

flow restriction means between said chamber and said infusion site;

means to control actuation of said positive displacement pump comprising;

programmed means to couple said source of power to said solenoid and thereby regulate the flow of fluid to said infusion site in accordance with a predetermined fluid delivery rate, and an external programmer programmed for varying actuation of said positive displacement pump, said programmer comprising;

a processor input means to provide instructions to said processor, memory means for storing data from said processor indicative of actuation rates for said positive displacement pump, means to transfer said data to said programmed means, a real time clock for providing a time input to said processor, a program memory and a non-volatile memory, and wherein said means to transfer data comprises a receiver/transmitter to establish a communication link with said programmed means.

2. The infusion system of claim 1, wherein said fluid reservoir comprises a housing, a bellows dividing said housing into a plurality of chambers, an inlet and outlet coupled to one of said chambers, said inlet including a self-sealing penetrable septum closing said inlet yet allowing said one chamber to be refilled by injection through the skin; the second of said chambers being charged with a volatile liquid to provide a vapor pressure of greater than one atmosphere at a physiological temperature of said living body.

3. The infusion system of claim 1, wherein said drug pressurant chamber comprises an expandable housing operatively connected to said positive displacement pump.

4. The infusion pump of claim 3, wherein said positive displacement pump comprises a solenoid and armature, said armature coupled to said drug pressurant chamber to vary the volume thereof as a function of armature displacement; means to bias said armature into a rest position to reduce the volume of said pumping chamber; and means to actuate said solenoid.

5. The infusion system of claims 1, wherein said valve means comprises a check valve and, means to seal said check valve at all times except when fluid is being drawn from said reservoir into said drug pressurant chamber.

6. The infusion system of claim 1, wherein said valve means comprises a check valve and, means to substantially seal said check valve but provide a predetermined continuous basal flow of fluid from said reservoir to said flow restriction.

7. The infusion system of claim 1, wherein said flow restriction means comprises a capillary tube housing a predetermined length for its internal diameter to establish a pressure drop as a function of the viscosity of the fluid passing therethrough.

8. The infusion system of claim 1, further comprising an outlet tube coupling said fluid reservoir to said drug pressurant chamber and having an internal size minimize any pressure drop there between.

9. The infusion system of claim 1, further comprising means to sense the pressure drop across said flow restriction means and, means responsive to said sensed pressure drop to provide an input signal to said positive displacement pump thereby changing its output.

10. An infusion system implantable in a living body comprising;

an infusion reservoir, an entry port having self-sealing means to allow said reservoir to be refilled with fluid by injection through the skin, said reservoir maintained at a positive pressure;

an outlet conduit from said infusion reservoir establishing a path of fluid communication between said reservoir and an infusion site in the body said outlet conduit including means to establish a flow restriction in said path;

a positive pressure pumping chamber disposed in said path of fluid communication between said reservoir and said flow restriction; means to vary the volume of said pumping chamber to thereby draw fluid from said reservoir and fill said chamber or to pressurize said chamber to expel fluid from said chamber to said infusion site; and check valve means in said flow path between said reservoir and said pumping chamber to prevent backflow of fluid from said chamber to said reservoir, said check valve including means to substantially seal and valve but provide a predetermined continuous basal flow of fluid from said reservoir to said outlet conduit.

11. The infusion system of claim 10, wherein said means to vary the volume of said pumping chamber comprises a solenoid and armature, said armature defining a pumping element operatively coupled to said pumping chamber to vary the volume thereof as a function of armature displacement; and means to bias said armature into a rest position to reduce the volume of said pumping chamber.

12. The infusion system of claim 11, further comprising means to actuate said solenoid.

13. The infusion system of claim 12, further comprising means to sense the displacement of said armature and provide a signal to said means to actuate said solenoid indicative of the flow rate to said infusion site.

14. The infusion system of claim 12, wherein said means to actuate said solenoid comprises a source of electrical power and switch means to couple said solenoid to said power source.

15. The infusion system of claim 12, further comprising means to determine a pressure differential existing across said flow restriction to provide a signal to said means to actuate said solenoid indicative of the flow rate to said infusion site.

16. The infusion system of claim 12, wherein said means to actuate said solenoid comprises a memory containing data indicative of predicted flow rates of said system, sensor means to provide input indicative of actual flow rates of said system, comparator means receiving said data and said input and generating an output error signal and means responsive to said output error signal to actuate said solenoid to vary the flow of fluid from said pumping chamber to said infusion site.

17. The infusion system of claim 10, wherein said check valve includes means to substantially seal said valve but provide a predetermined continuous basal flow or fluid from said reservoir to said outlet conduit.

18. An infusion system for implantation in a living body comprising;

a fluid reservoir maintaining a liquid under positive pressure for delivery to an infusion site;

a drug pressurant chamber receiving fluid from said fluid reservoir;

a positive displacement pump to vary the volume of said drug pressurant chamber and thereby either fill said chamber by increasing its volume or pressurize said chamber to expel fluid from said chamber by reducing its volume;

valve means interposed between said reservoir and said chamber to prevent backflow of said fluid into said reservoir; said valve means comprising a check valve and, means to substantially seal said check valve but provide a predetermined continuous basal flow of fluid from said reservoir to said flow restriction; and flow restriction means between said chamber and said infusion site.

19. The infusion system of claim 18, further comprising means to control actuation of said positive displacement pump.

20. The infusion system of claim 19, wherein said means to control actuation of said positive displacement pump comprises programmed means to couple said source of power to said solenoid and thereby regulate the flow of fluid to said infusion site in accordance with a predetermined fluid delivery rate.

21. The infusion system of claim 20 further comprising an external programmer said programmed means for varying actuation of said positive displacement pump.

22. The infusion system of claim 21 wherein said programmer comprises: a processor, input means to provide instructions to said processor, memory means for storing data from said processor indicative of actuation rates for said positive displacement pump, and means to transfer said data to said programmed means.

23. The infusion system of claim 22 wherein said programmer further comprises a real time clock for providing a time input to said processor, a program memory and a non-volatile memory, and wherein said means to transfer data comprises a receiver/transmitter to establish a communication link with said programmed means.

* * * * *